US00PP27579P3

(12) United States Plant Patent
Ranney

(10) Patent No.: US PP27,579 P3
(45) Date of Patent: Jan. 24, 2017

(54) HYBRID FLOWERING CHERRY TREE NAMED 'NCPH1'

(50) Latin Name: ***Prunus* sp.**
Varietal Denomination: NCPH1

(71) Applicant: North Carolina State University, Raleigh, NC (US)

(72) Inventor: Thomas G. Ranney, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 84 days.

(21) Appl. No.: 14/544,707

(22) Filed: Feb. 6, 2015

(65) Prior Publication Data

US 2016/0234987 P1 Aug. 11, 2016

(51) Int. Cl.
*A01H 5/00* (2006.01)

(52) U.S. Cl.
USPC ..... Plt./182

(58) Field of Classification Search
USPC ..... Plt./156, 181, 182, 216
See application file for complete search history.

(56) References Cited

PUBLICATIONS

J. Frank Schmidt and Son Co., JFS Introductions, Pink Cascade Cherry website (http://www.jfschmidt.com/introductions/pinkcascade/index.html). 1 page.*
USPTO-TM search for Pink Cascade. Accessed on Apr. 14, 2016. 2 pages.*
J. Schmidt & Son Co., *Trees are the Answer*, 2014-2015 Price Guide.
J. Frank Schmidt & Son Co. "Trees are the Answer", published May 2014, http://www.jfschmidt.com/pdfs/JFS_New_2015.pdf.
J. Frank Schmidt & Son Co., published May 2014, http://www.jfschmidt.com/pdfs/pinkcascadecherry.pdf.

* cited by examiner

*Primary Examiner* — Susan McCormick Ewoldt
*Assistant Examiner* — Karen Redden
(74) *Attorney, Agent, or Firm* — Myers Bigel, P.A.

(57) ABSTRACT

'NCPH1' is a new cultivar of hybrid cherry tree with a strict weeping habit, small stature, and showy pink flowers.

3 Drawing Sheets

Latin name of the genus and species: The Latin name of the novel plant variety disclosed herein is *Prunus* sp.

Variety denomination: The inventive hybrid of *Prunus* 'Snofozam'×*Prunus* 'First Lady' disclosed herein has been given the varietal denomination 'NCPH1'.

BACKGROUND OF THE INVENTION

The present invention comprises a new and distinct hybrid cherry cultivar hereinafter referred to by the cultivar name 'NCPH1'. This new cherry was developed through a breeding program at North Carolina State University, Mills River, N.C. 'NCPH1' was selected from a population of seedlings grown from a controlled cross of *Prunus* 'Snofozam' Snow Fountains® NCSU 2007-040 (unpatented, female parent)× *Prunus* 'First Lady' NCSU 2005-151 (unpatented, male parent). The first asexual propagation of 'NCPH1' was carried out in July 2010 by rooting stem cuttings in Mills River, N.C. and has been asexually reproduced repeatedly by vegetative cuttings over a 3 year period. 'NCPH1' roots readily from softwood cuttings treated with a basal dip of 4,000-5,000 ppm indole butyric acid (potassium salt) in water. 'NCPH1' has been found to retain its distinctive characteristics through successive asexual propagations.

SUMMARY OF THE INVENTION

The following are the unique combination of characteristics of this new cultivar when grown under standard horticultural practices in Mills River, N.C.

1. Small stature.
2. Strict weeping habit.
3. Pink flower color.

BRIEF DESCRIPTION OF THE DRAWINGS

This new cherry is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new hybrid cherry.

DETAILED BOTANICAL DESCRIPTION

Figure 1:
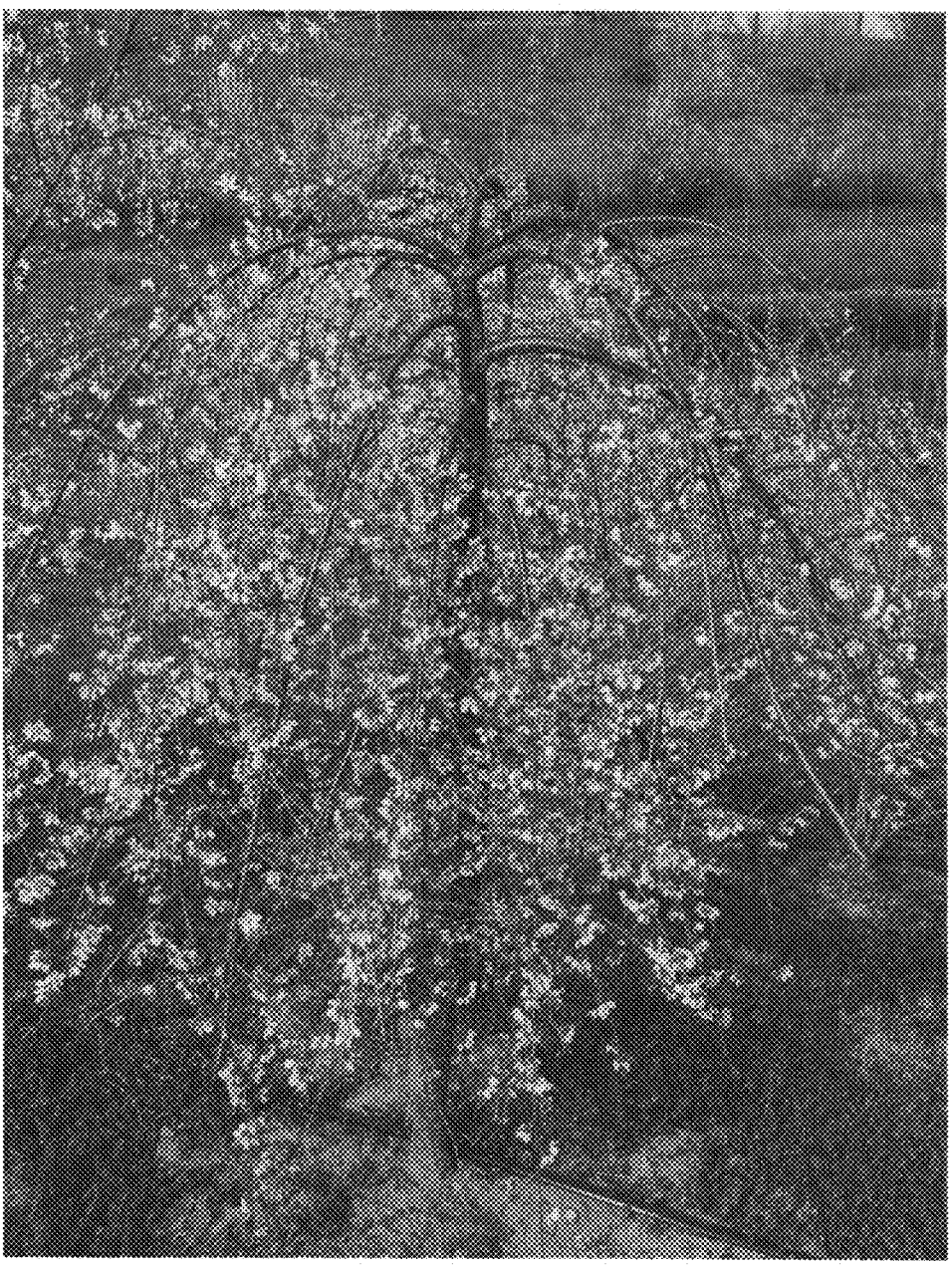
FIG. 1 is a color photograph showing the form and flowers of 'NCPH1' in spring 2011 on a three-year-old tree.
Figure 2:
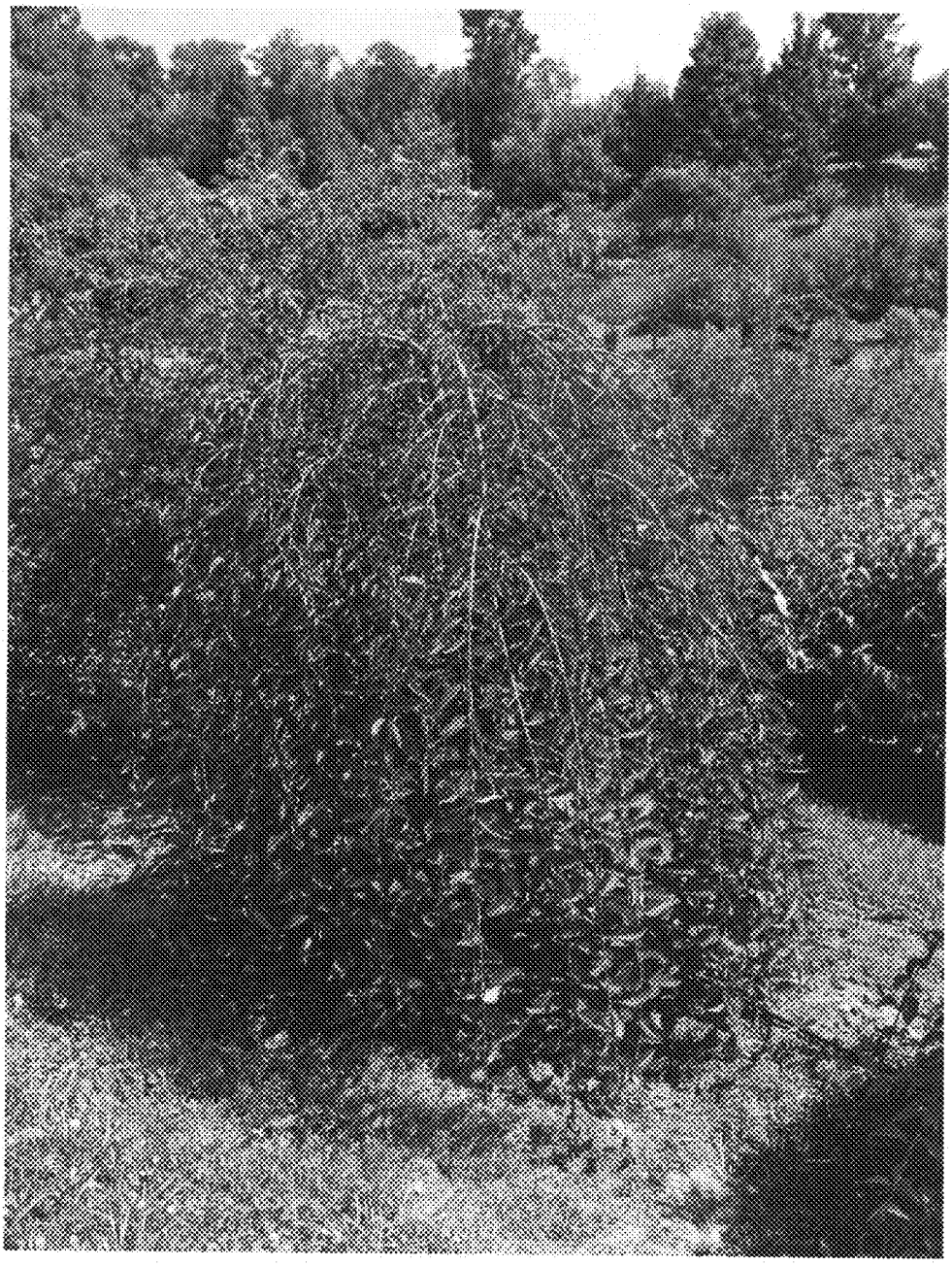
FIG. 2 is a color photograph showing the form and foliage of 'NCPH1' in summer 2010 on a two-year-old tree (third growing season).
Figure 3:
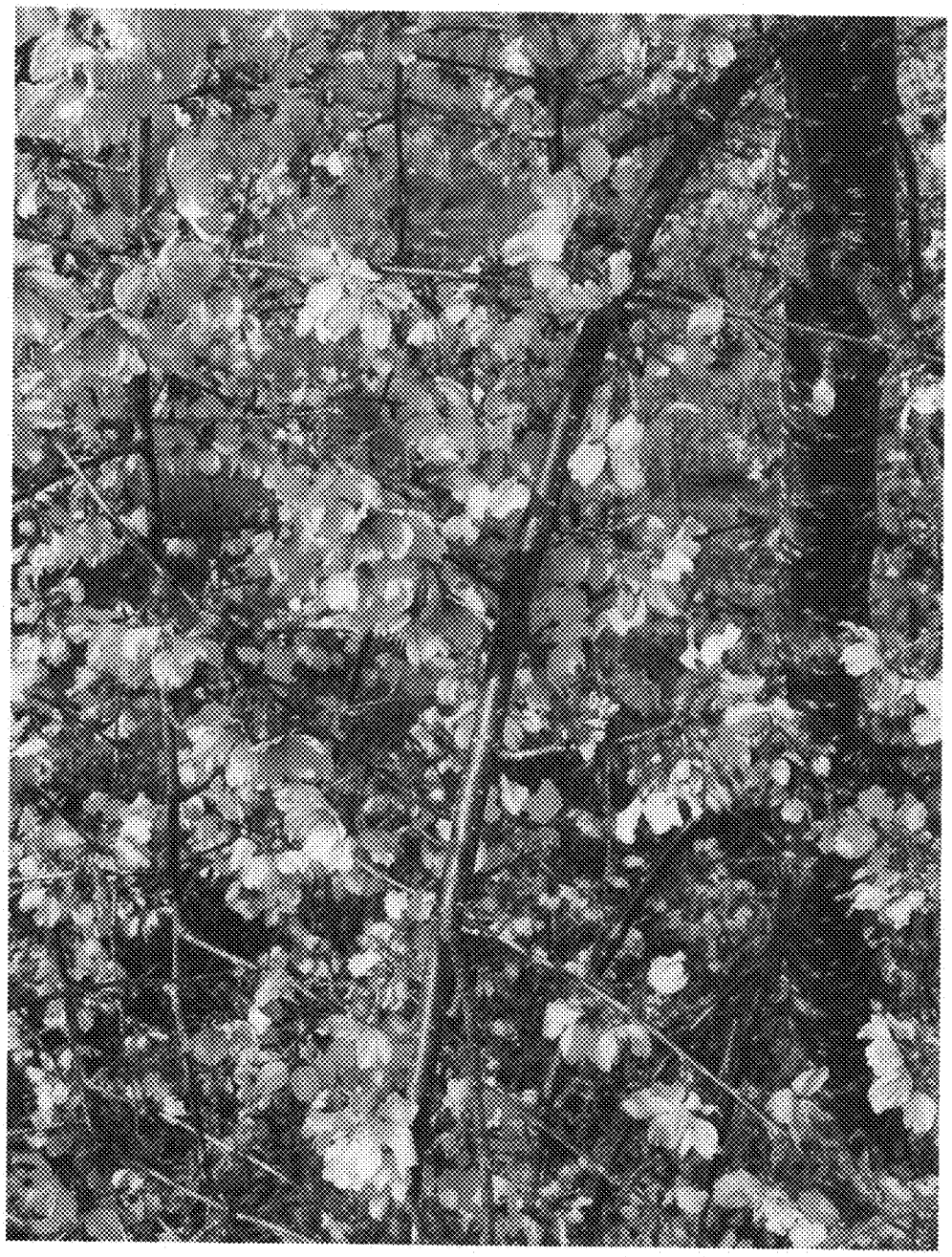
FIG. 3 is a color photograph of inflorescences of 'NCPH1' in spring 2011 on a three-year-old tree.

The following is a detailed description of the botanical characteristics of the new and distinct hybrid cherry variety plant known by the denomination 'NCPH1'. The detailed description was taken on a five-year-old field-grown plant in Mills River, N.C. in 2013. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

Technical Description of the Variety.

Classification:

*Botanical name.*—*Prunus* 'NCPH1'.

*Common name.*—Hybrid flowering cherry.

Parentage: Seedling grown from a controlled cross of *Prunus* 'Snofozam' NCSU 2007-040 (unpatented)× *Prunus* 'First Lady' NCSU 2005-151 (unpatented).

Plant description:

*Growth habit.*—Strongly pendulous with a small stature.

*Height.*—Variable. Must be staked initially to develop a tree form. Can reach 2 to 3 m in five years.

*Width.*—2 to 3 m after five years.

Shoot and stem:

*Immature shoot texture (current year).*—Glabrous.

*Immature shoot color (current year).*—Yellow-Green (145B) to Greyed-Red (178A).

*Branch (shoot) length.*—Ranging from 15 cm (laterals) to 80 cm (terminals).

*Branch (shoot) diameter.*—3-6 mm.

*Mature stem texture (from prior year).*—Glabrous, with prolific corky lenticels.

*Mature stem color (from prior year).*—Brown (N200B) with lenticels Brown (N200D).

*Trunk diameter.*—13 cm as measured 30 cm from the ground on an 8-year old tree.

*Trunk texture.*—Covered with prominent corky horizontal lenticels and small patches of exfoliating outer bark.

*Trunk color.*—Outermost bark layer is Brown (N200B) with the inner bark layer Greyed-Purple (N186C).

*Trunk shape.*—Cylindrical.

*Trunk lenticels.*—Color: Greyed-Orange (163A).

Branching: Long weeping, branching from the main stem.

Roots: Fibrous, freely branching.

Leaves:

*Type.*—Simple.

*Persistence.*—Deciduous.

*Arrangement.*—Alternate.

*Shape.*—Elliptical to lanceolate.

*Apex.*—Acuminate.

*Base.*—Acute to oblique.

*Venation pattern.*—Pinnate/Reticulate.

*Vein color.*—Upper: Green (137B). Lower: Green (137B).

*Margins.*—Biserrate.

*Emerging leaves.*—Color: Upper: Yellow-Green (144A). Lower: Yellow-Green (146C). Texture: Scaberulose with sparse stiff pubescence along veins on both sides.

*Mature leaves during growing season.*—Color: Upper: Green (137B). Lower: Green (137C). Texture: Scaberulose with sparse stiff pubescence along veins on both sides. Length of lamina: Avg. 65.5 mm (47.4 to 79.3 mm). Width: Avg. 26.9 mm (17.1 to 35.2 mm).

*Fall foliage color.*—Before frost foliage senesces to Greyed-Orange (163B and 163A) (upper and lower surfaces). After frost any green foliage turns Greyed-Purple (187A) and then to Brown (200A) (upper and lower surfaces).

*Leaf attachment.*—Petiolate.

*Petiole.*—Length: Avg. 8.2 mm (7.8 to 12.1 mm). Diameter: Avg. 0.96 mm (0.8 to 1.4 mm). Color: Yellow-Green (145B) darkening to Greyed-Red (178A). Texture: Puberulent.

*Stipule.*—Deeply dissected stipules, Green (137B). Avg 19.5 mm (17.4 to 21.1 mm) long and avg. 7.1 mm (4.8 to 10.2 mm) wide.

Inflorescence:

*Description.*—Single flowers.

*Number of true flowers per inflorescence.*—1 to 4 (most typically in pairs).

*Flowering season.*—Spring; March and April in Mills River, NC.

*Fragrance.*—Slight fragrance.

*Bud.*—Shape: Elongated ovoid. Length: Avg 11.9 mm, Range (9.4 to 16.1 mm). Diameter: Avg 4.7 mm, Range (3.8 to 6.3 mm). Color: Red-Purple (63C).

*Perianth.*—Diameter at anthesis: Avg. 27.5 mm (25 to 30 mm). Height at anthesis: Avg. 17.5 mm, Range (16 to 19 mm).

*Perianth aspect.*—Clustered, mostly outward facing.

*Petal.*—Arrangement: Whorl. Number: 5. Fused: Not fused. Texture: Smooth. Shape: Ovate. Margin: Undulate. Apex: Notched. Length: Avg. 12.9 mm, Range (11.6 to 14.8 mm). Width: Avg. 10.1 mm, Range (9.1 to 11 mm). Color when opening: Upper: Red-Purple (65A) with veins Red-Purple (67A). Lower: Red-Purple (65A) with veins Red-Purple (67A). Color at anthesis: Upper: Varies from flower to flower. Purple (73B), Purple (73D) with veins of Red-Purple (67A) or veins are indistinguishable from petal. Lower: Varies from flower to flower. Purple (73B), Purple (73D) with veins of Red-Purple (67A) or veins are indistinguishable from petal. Color fading to: Close to Purple (75A).

*Calyx.*—Shape: Five-lobed conic tube. Length: Avg. 9.6 mm, range (7.5 to 12.1 mm). Diameter: Avg. 10.4 mm, range (9.2 to 11.2 mm).

*Sepal.*—Appearance: Fused base surrounding a superior ovary with five acute, entire margin, lanceolate lobes. Number: 5. Color, immature: Upper: Closest to Green (139B) with Red-Purple (59B) highlights. Lower: Closest to Green (139B) with Red-Purple (59B) highlights. Color, mature: Upper: Greyed-Purple (183B). Lower: Red-Purple (59A). Texture: Puberulent. Length: Avg. 3.5 mm, range (3.0 to 4.0 mm). Width: Avg. 3.1 mm, Range (2.3 to 3.4 mm).

*Peduncle.*—Length: Avg. 11.1 mm (8.6 to 14 1 mm). Diameter: Avg. 0.87 mm (0.76 to 1.11 mm). Color: Green (137D). Surface texture: Puberulent.

Reproductive organs:

*Gynoecium.*—Pistil number: 1. Pistil length: Avg. 12 4 mm (10.7 to 14.2 mm). Stigma shape: Flattened, irregularly globoid. Stigma color: 138C (Green). Style length: Avg. 10.1 mm (9.5 to 10.9 mm). Style color: Green (138D) blushed with Red-Purple (65A) darkening with age to Red-Purple (67A). Ovary shape: Oval. Ovary color: Green (138D).

*Androcoecium.*—Stamen number: Avg. 31 (29 to 33). Anther shape: Ovoid to reniform. Anther attachment: Dorsifixed. Anther size: Avg. 0.53 mm (0.35 to 0.8 mm). Anther color: Yellow (13A). Filament color: White (N155A) senescing to Red-Purple (61A). Amount of pollen: Normal amount for genus. Pollen color: Yellow (13A).

*Fruit and seed.*—Fruit type: Drupe. Fruit texture: Glabrous and shiny. Fruit length: Avg. 9.5 mm (8.7 to 10.2 mm). Fruit diameter: Avg. 9.3 mm (8.3 to 10.3 mm). Fruit color: Immature: Yellow-Green (146C). Mature: Closest to Greyed-Purple (N186A). Seed number: 1 seed per fruit. Seed length: Avg. 6.2 mm (5.9 to 6.8 mm). Seed diameter: Avg. 5 mm (4.6 to 5 6 mm). Seed color: Greyed-Orange (165C).

Disease and insect resistance: No significant disease or insect pests have been observed.

Cold hardiness: At least USDA zone 6b; testing has not been completed in colder zones.

COMPARISON OF 'NCPH1' WITH COMMERCIAL CULTIVARS AND PARENTAL PLANTS

'NCPH1' is distinguished from *Prunus* 'First Lady' by its strict weeping habit and lighter red-purple (73B-73D) petals compared to the upright, ascending form and darker red-purple (67B-67C) petals of 'First Lady'.

Table 1 shows distinguishing characteristics between 'NCPH1' and commercial cultivars. 'NCPH1' is distinguished from *Prunus* 'Snofozam' in that 'NCPH1' has pink flowers, which are larger with a slight fragrance, and smaller leaves. 'NCPH1' is distinguished from *Prunus subhirtella* 'Pendula Plena Rosea' by having a smaller stature, a strict weeping habit, smaller leaves, simple rather than double flowers, and wider petals.

TABLE 1

Comparison to commercial cultivars.

| | Taxa | | |
|---|---|---|---|
| Trait | *Prunus* 'Snofozam' | *Prunus subhirtella* 'Pendula Plena Rosea' | *Prunus* 'NCPH1' |
| Plant height | 2 to 3 m (dependent upon training or grafting height) | 5 to 8 m | 2 to 3 m (dependent upon training or grafting height) |
| Plant habit | Strictly weeping | Arching branches, with pendulous shoot tips. | Strictly weeping |
| Flower diameter | Avg 25.0 mm (22 to 28 mm) | Avg 27.0 mm (24.0 to 29.0 mm) | Avg 27.5 mm (25.0 to 30.0 mm) |
| Fragrance | None | None | Slight |
| Flower type | Simple | Double | Simple |
| Petal color | Closest to White (N155B), occasionally blushed Purple (75C) | Varies from petal to petal, Purple (76D) and Purple (76B) | Varies from flower to flower, Purple (73B), Purple (73D) with veins or Red-Purple (67A) or veins are indistinguishable from petal |
| Petal size | | | |
| Length | Avg 14.5 mm (14.3 to 14.9 mm) | Avg 11.6 mm (9.5 to 14.4 mm) | Avg 12.9 mm (11.6 to 14.8 mm) |
| Width | Avg 9.1 mm (8.4 to 9.7 mm) | Avg 6.5 mm (4.9 to 8.4 mm) | Avg 10.1 mm (9.1 to 11 mm) |
| Leaf size | | | |
| Length | Avg 84.2 mm (54.4 to 102.4 mm) | Avg 93.9 mm (78.7 to 108.5 mm) | Avg 65.5 mm (47.4 to 79.3 mm) |
| Width | Avg 40.2 mm (29.9 to 49.0 mm) | Avg 36.4 mm (31.7 to 40.5 mm) | Avg 26.9 mm (17.1 to 35.2 mm) |

What is claimed is:

1. A new and distinct hybrid cherry tree named 'NCPH1' substantially as illustrated and described herein.

* * * * *